United States Patent [19]

Drent

[11] Patent Number: 5,124,300

[45] Date of Patent: Jun. 23, 1992

[54] CARBONYLATION CATALYST SYSTEM

[75] Inventor: Eit Drent, Amsterdam, Netherlands

[73] Assignee: Shell Oil Company, Houston, Tex.

[21] Appl. No.: 650,352

[22] Filed: Feb. 4, 1991

[30] Foreign Application Priority Data

Feb. 5, 1990 [GB] United Kingdom ................. 9002521

[51] Int. Cl.$^5$ .............................................. B01J 31/04
[52] U.S. Cl. .................................. 502/167; 502/166;
560/232; 560/233
[58] Field of Search ................ 502/167, 166, 161, 159

[56] References Cited

FOREIGN PATENT DOCUMENTS 106379 8/1983 European Pat. Off. .
186228 11/1985 European Pat. Off. .
235864 2/1987 European Pat. Off. .
259914 8/1987 European Pat. Off. .
271144 11/1987 European Pat. Off. .
274795 12/1987 European Pat. Off. .
279477 1/1988 European Pat. Off. .
282142 3/1988 European Pat. Off. .
305012 8/1988 European Pat. Off. .

Primary Examiner—Patrick P. Garvin

[57] ABSTRACT

A catalyst system, which comprises:
a) a source of a Group VIII metal;
b) a phosphine having an aromatic substituent which contains an imino nitrogen atom;
c) a source of protons; and
d) a tertiary amine.

6 Claims, No Drawings

CARBONYLATION CATALYST SYSTEM

FIELD OF THE INVENTION

The present invention relates to a novel catalyst system comprising a tertiary amine and to its use in the carbonylation of acetylenically and olefinically unsaturated compounds.

BACKGROUND OF THE INVENTION

Many processes are known in the art for the carbonylation of acetylenically and olefinically unsaturated compounds. A review of such processes is provided by J. Falbe, "New Syntheses with Carbon Monoxide", Springer-Verlag, Berlin Heidelberg New York, 1980. Typically, the processes involve the reaction of an acetylenically or olefinically unsaturated compound with carbon monoxide and, in some cases, a nucleophilic compound having a removable hydrogen atom, in the presence of a carbonylation catalyst system. In many instances, the carbonylation catalyst system comprises a source of a Group VIII metal and a ligand such as a phosphine.

Recently, several processes for the carbonylation of acetylenically and olefinically unsaturated compounds have been disclosed which involve the use of a carbonylation catalyst system comprising a Group VIII metal compound, in particular a palladium compound, a phosphine and a protonic acid. The processes proceed with a remarkably high reaction rate.

European Patent Nos. EP-A1-106379. EP-A1-235864. EP-A1-274795 and EP-A1-279477 disclose processes for the carbonylation of olefinically unsaturated compounds in which a catalyst system comprising a palladium compound, a triarylphosphine and a protonic acid is used. In all of the examples, the triarylphosphine used is a triphenylphosphine.

European Patent No. EP-A1-0186228 discloses a process for the carbonylation of acetylenically unsaturated compounds in which a catalyst system comprising a palladium compound, a phosphine and a protonic acid is used. The examples illustrate the use of optionally substituted hydrocarbyl phosphines such as triphenylphosphine.

More recently, several processes for the carbonylation of acetylenically and olefinically unsaturated compounds have been disclosed which involve the use of a catalyst system comprising a palladium compound, a pyridylphosphine and an acid.

European Patent Nos. EP-A1-259914, EP-A1-282142 and EP-A1-305012 disclose processes for the carbonylation of olefinically unsaturated compounds in which a catalyst system comprising a palladium compound, a pyridylphosphine and a protonic acid is used.

European Patent No. EP-A1-0271144 discloses a process for the carbonylation of an acetylenically unsaturated compound in which a catalyst system comprising a palladium compound a pyridylphosphine and a protonic acid is used.

None of the aforementioned European patent specifications disclose catalyst systems which additionally comprise a tertiary amine, nor do they suggest that such catalyst systems would be of interest in the carbonylation of acetylenically and olefinically unsaturated compounds. Tertiary amines are basic compounds and so might be expected to have a marked inhibitory effect upon the performance of the acid-containing catalyst system. Indeed, the Applicants have found that the performance of triarylphosphine-based catalyst systems is markedly impaired in the carbonylation of olefins when a tertiary amine is included.

It, however, has now been found that acetylenically and olefinically unsaturated compounds can be carbonylated at a good reaction rate using a catalyst system comprising a palladium compound, a pyridylphosphine, a protonic acid and a tertiary amine.

SUMMARY OF THE INVENTION

The present invention therefore provides a catalyst system which comprises:
  a) a source of a Group VIII metal;
  b) a phosphine having an aromatic substituent which contains an imino nitrogen atom;
  c) a protonic acid; and
  d) a tertiary amine.

DESCRIPTION OF THE PREFERRED EMBODIMENTS

Catalyst systems according to the invention have been found to be highly active in the carbonylation of acetylenically and olefinically unsaturated compounds. This finding is very surprising and is technically important because it means that acetylenically and olefinically unsaturated compounds can be carbonylated using the highly active Group VIII metals/pyridylphosphine/protonic acid catalyst systems under basic conditions. Many reactions which can only be satisfactorily performed under basic conditions are now possible. For example, it has been found that esters of acid-sensitive hydroxy compounds such as silanols and tertiary alcohols may be prepared in good selectivity using catalyst systems according to the invention.

It has also been found that catalyst systems according to the invention exhibit improved tolerance of allenes, which are common impurities of acetylenically unsaturated compounds.

Still further, it has been found that alkoxymethoxyalkanoates may be prepared by carbonylating alkenes with alkanols and formaldehyde in the presence of a catalyst system according to the invention.

Yet further it has been found that catalyst systems according to the invention have prolonged stability compared with corresponding systems which lack a tertiary amine.

The catalyst system according to the invention comprises a source of a Group VIII metal. The source of a Group VIII metal may be the metallic element or, preferably, a Group VIII metal compound.

Examples of Group VIII metals are iron cobalt, nickel, ruthenium, rhodium, palladium, iridium and platinum.

The catalyst system according to the invention preferably comprises a source of a palladium compound.

Examples of compounds of Group VIII metals include salts, for example, salts of nitric acid; sulfuric acid; sulfonic acids; phosphonic acids; perhalic acids; carboxylic acids such as alkane carboxylic acids having not more than 12 carbon atoms, e.g. acetic acid; and hydrohalic acids. Since halide ions can be corrosive, salts of hydrohalic acids are not preferred. Other examples of compounds of Group VIII metals include complexes, such as complexes with acetylacetonate, phosphines and/or carbon monoxide. For example the compound of a Group VIII metal may be palladium acetylacetonate, tetrakis-triphenylphosphinepalladium, bis-tri-o- tolylphosphinepalladium acetate, bis-diphenyl-2-pyridylphosphinepalladium acetate, tetrakis-diphenyl-2-pyridylphosphinepalladium, bis-di-o-tolylpyridylphosphinepalladium acetate, or bis-diphenylpyridylphosphinepalladium sulphate.

The catalyst system used in the process according to the invention further comprises a phosphine having an aromatic substituent which contains an imino nitrogen atom.

As used herein, the term "imino nitrogen atom" means a nitrogen atom which may be represented in the structural formula of the aromatic substituent containing it by the formula

For example, if the aromatic substituent is a pyridyl group, the structural formula of the aromatic substituent is

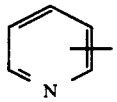

The phosphine preferably comprises one or two phosphorus atoms. Each phosphorus atom has three substituents. At least one of these substituents is an aromatic substituent which contains an imino nitrogen atom. The remaining substituents are preferably selected from optionally substituted aliphatic and aromatic hydrocarbyl groups. When the phosphine comprises more than one phosphorus atom, it is possible for one substituent to be shared by more than one phosphorus atom, as for example in

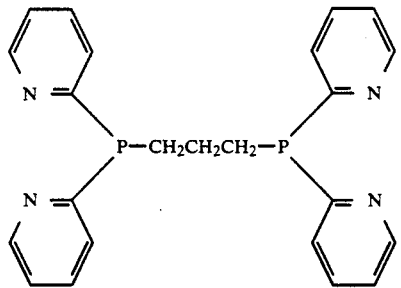

The aromatic substituent which contains an imino nitrogen is preferably a 6-membered ring containing one, two or three nitrogen atoms. The aromatic substituent may itself be optionally substituted.

When a substituent is said to be "optionally substituted" in this specification, unless otherwise stated, the substituent may be unsubstituted or substituted by one or more substituents. Examples of suitable substituents include halogen atoms; alkyl groups; alkoxy groups; haloalkyl groups; haloalkoxy groups; acyl groups; acyloxy groups; amino groups, preferably alkyl or dialkylamino groups; hydroxy groups; nitrile groups; arylamino groups; and aromatic hydrocarbyl groups.

An aliphatic hydrocarbyl group is preferably an alkyl group, for example a $C_{1-4}$ alkyl group; or a cycloalkyl group, for example a $C_{3-6}$ cycloalkyl group.

An aromatic hydrocarbyl group is preferably a phenyl group.

A halogen atom, as such or in a haloalkyl group, is preferably a fluorine, chlorine or bromine atom.

An acyl group in an acyl, acyloxy or acylamino group is preferably a $C_{2-5}$ alkanoyl group such as acetyl.

Examples of aromatic substituents containing an imino nitrogen atom are pyridyl, pyrazinyl, quinolyl, isoquinolyl, pyrimidinyl, pyridazinyl, cinnolinyl, triazinyl, quinoxalinyl, and quinazolinyl. Preferred substituents are pyridyl and pyrimidyl.

An imino group in an aromatic substituent containing an imino nitrogen atom is preferably connected to a phosphorus atom through a single bridging carbon atom. For example, if the aromatic substituent is a pyridyl group, it is preferably connected through the carbon atom at the 2-position in the pyridyl group. Accordingly, examples of preferred aromatic substituents containing an imino nitrogen atom are 2-pyridyl; 2-pyrazinyl; 2-quinolyl; 1-isoquinolyl; 3-isoquinolyl; 2-pyrimidinyl; 3-pyridazinyl; 3-cinnolinyl; 2-triazinyl; 2-quinoxalinyl; and 2-quinazolinyl; 2-Pyridyl, 2-pyrimidyl and 2-triazinyl are particularly preferred.

When the phosphine contains one phosphorus atom, it may conveniently be represented by the general formula

 (I)

in which $R^1$ represents an aromatic substituent containing an imino nitrogen atom, and $R^2$ and $R^3$, which may be the same or different, represent a group $R^1$ or an optionally substituted aliphatic or aromatic hydrocarbyl group.

Particularly preferred phosphines are:
bisphenyl-(2-pyridyl)phosphine,
bis(2-pyridyl)phenylphosphine,
tris(2-pyridyl)phosphine,
diphenyl(6-methoxy-2-pyridyl)phosphine,
bis(6-ethoxy-2-pyridyl)phenylphosphine,
bis(6-chloro-2-pyridyl)phenylphosphine,
bis(6-bromo-2-pyridyl)phenylphosphine,
tris(6-methyl-2-pyridyl)phosphine,
bis(6-methyl-2-pyridyl)phenylphosphine,
bisphenyl(6-methyl-2-pyridyl)phosphine,
bis(3-methyl-2-pyridyl)phenylphosphine,
bisphenyl(4,6-dimethyl-2-pyridyl)phosphine,
di(n-butyl)-2-pyridylphosphine,
dimethyl-2-pyridylphosphine,
methyl phenyl-2-pyridylphosphine,
n-butyl tert-butyl 2-pyridylphosphine,
n-butyl(4-methoxyphenyl)(2-pyridyl)phosphine, and
methyl di(2-pyridyl)phosphine.

The catalyst system used in the process according to the invention further comprises a protonic acid. The function of the protonic acid is to provide a source of protons. Accordingly, the protonic acid may be generated in situ.

Preferably, the protonic acid is selected from acids having a non-coordinating anion. Examples of such acids include sulfuric acid; a sulfonic acid, e.g. an optionally substituted hydrocarbylsulfonic acid such as benzenesulfonic acid, p-toluenesulfonic acid, naphthalenesulfonic acid; an alkylsulfonic acid such as methanesulfonic acid or tert-butylsulfonic acid, or 2-hydroxypropanesulfonic acid, trifluoromethanesulfonic acid, chlorosulfonic acid or fluorosulfonic acid; a phosphonic acid, e.g. orthophosphonic acid, pyrophosphonic acid or benzenephosphonic acid; a carboxylic acid, e.g. chloroacetic acid, dichloroacetic acid, trichloroacetic acid, trifluoroacetic acid, oxalic acid or terephthalic acid; or a perhalic acid such as perchloric acid. The protonic acid may also be an acidic ion exchange resin.

The catalyst system used in the process according to the invention may be homogeneous or heterogeneous. Preferably, it is homogeneous.

The ratio of the number of moles of phosphine per gram atom of Group VIII metal is not critical. Preferably, it is in the range of from 1 to 1000, more preferably from 2 to 500, especially from 10 to 100.

The ratio of the number of moles of phosphine per mole of protonic acid is not critical. The function of the protonic acid is to provide a source of protons. Accordingly, the protonic acid may be generated in situ. Preferably, it is in the range of from 0.1 to 50, more preferably from 0.5 to 5.

Examples of tertiary amines include optionally substituted aromatic, heterocyclic tertiary amines such as pyridines, quinolines, isoquinolines, pyrimidines, pyrazines, triazoles, triazines, pyridazines, purines, thiazoles, benzimidazoles, oxazoles, pyrazoles and isothiazoles; aliphatic tertiary amines such as dialkylamines e.g. dimethylamine or diethylamine; and optionally substituted tertiary anilines such as, N,N-dialkylanilines, e.g. N,N-dimethylaniline.

Preferably, the tertiary amine is a pyridine or an N,N-dialkylaniline.

Preferred examples of pyridines are pyridine alkyl-substituted pyridines such as 2,6-dimethylpyridine and polyvinylpyridine.

The number of equivalent of tertiary amine present per mole of protons is preferably at least 0.5, more preferably, at least 1, even more preferably, at least 2, especially at least 5. Depending upon the particular carbonylation process in which the catalyst system is to be used, the tertiary amine is preferably present in catalytic quantities or in solvent quantities.

When the tertiary amine is present in catalytic quantities, the number of equivalent of tertiary amine per mole of protons is preferably in the range of from 0.1 to 200, more preferably, 0.5 to 100, especially 1 to 50.

When the tertiary amine is present in solvent quantities, the number of equivalents of tertiary amine per mole of protons is preferably in the range of from 1 to 2,500, more preferably 1.5 to 1500, especially 10 to 1000.

For the avoidance of doubt, the tertiary amine may not be a phosphine, for example the phosphine having an aromatic substituent containing an imino nitrogen atom.

As has been stated above, it has been found that compositions according to the invention have good activity in the carbonylation of unsaturated hydrocarbons.

Accordingly, the invention further provides the use of a catalyst system as defined hereinbefore in the carbonylation of an acetylenically or olefinically unsaturated hydrocarbon.

According to another aspect, the invention provides a process for the carbonylation of an acetylenically or olefinically unsaturated compound, which comprises reacting an acetylenically or olefinically unsaturated compound with carbon monoxide in the presence of a catalyst system as defined above.

The acetylenically or olefinically unsaturated compound is preferably an asymmetric acetylene or olefin, most preferably an alpha acetylene or olefin.

An olefinically unsaturated compound is preferably a substituted or unsubstituted alkene or cycloalkene having from 2 to 30, preferably from 3 to 20 carbon atoms per molecule.

An acetylenically unsaturated compound is preferably a substituted or unsubstituted alkyne having from 2 to 20, especially from 3 to 10 carbon atoms per molecule.

The acetylenically or olefinically unsaturated compound may contain one or more acetylenic or olefinic bonds, for example one, two or three acetylenic or olefinic bonds.

An olefin or acetylene may be substituted by, for example, a halogen atom, a cyano group, an acyl group such as acetyl, an acyloxy group such as acetoxy, an amino group such as dialkylamino, an alkoxy group such as methoxy, a haloalkyl group such as trifluoromethyl, a haloalkoxy group such as trifluoromethoxy, an amido group such as acetamido, or a hydroxy group. Some of these groups may take part in the reaction, depending upon the precise reaction conditions. For example, lactones may be obtained by carbonylating certain acetylenically unsaturated alcohols, for example 3-butyn-1-ol, 4-pentyn-1-ol or 3-pentyn-1-ol. Thus 3-butyn-1-ol may be converted into α-methylene-γ-butyrolactone.

Examples of alkynes are: ethyne, propyne, phenylacetylene, 1-butyne, 2-butyne, 1-pentyne, 1-hexyne, 1-heptyne, 1-octyne, 2-octyne, 4-octyne, 1.7-octadiyne, 5-methyl-3-heptyne, 4-propyl-2-pentyne, 1-nonyne, benzylethyne and cyclohexylethyne.

Examples of alkenes are: ethene, propene, phenylethene, 1-butene, 2-butene, 1-pentene, 1-hexene, 1-heptene, 1-octene, 2-octene, 4-octene. cyclohexene and norbornadiene.

The acetylenically or olefinically unsaturated compound can be both an acetylene and an olefin, for example as in 3-methyl-but-3-ene-2-yne.

It has been found that catalyst systems according to the invention are highly selective for acetylenic groups in the presence of olefinic groups.

The unsaturated compound may be carbonylated alone or in the presence of other reactants, for example, hydrogen or a nucleophilic compound having a removable hydrogen atom. An example of a nucleophilic compound having a removable hydrogen atom is a hydroxyl-containing compound.

A hydroxyl-containing compound is preferably an alcohol, water, a carboxylic acid or a silanol.

The ability of the catalyst systems according to the invention to carbonylate silanols is particularly surprising.

Any alcohol used may be aliphatic, cycloaliphatic or aromatic and may carry one or more substituents. The alcohol preferably comprises up to 20 carbon atoms per molecule. It may be, for example, an alkanol, a cycloalkanol or a phenol. One or more hydroxyl groups may be present, in which case several products may be formed, depending on the molar ratio of the reactants used.

Examples of alkanols include methanol, ethanol, 1-propanol, 2-propanol, 1-butanol, 2-butanol, 2-methylpropan-1-ol, and 2-methylpropan-2-ol.

Examples of phenols include phenol, alkylphenols, catechols, and 2,2-bis(4-hydroxyphenyl)propane.

Other examples of alcohols include polyvalent alcohols, in particular lower sugars such as glucose, fructose, mannose, galactose, sucrose, aldoxose, aldopentose, altrose, allose, talose, gulose, idose, ribose, arabonose, xylose, lyxose, erythrose or threose, cellulose, benzyl alcohol, 2,2-bis(hydroxymethyl)-1-butanol, stearyl alcohol, cyclohexanol, ethylene glycol, 1,2-propanediol, 1,4-butanediol, polyethyleneglycol, glycerol and 1,6-hexanediol.

An interesting reaction has been found to take place when an olefin is carbonylated with an alkanol and formaldehyde in the presence of the catalyst system according to the invention. Without wishing to be bound by any theory it is believed that the alcohol and formaldehyde react together to generate a hemiacetal. The hemiacetal, which is a hydroxyl-containing compound, then reacts with the olefin to afford an alkyloxymethyl alkanoate. For example, ethene, carbon monoxide, formaldehyde and methanol may be reacted together to afford methoxymethyl propionate.

The process according to the present invention can be carried out using a wide variety of carboxylic acids. For example, the carboxylic acids may be aliphatic, cycloaliphatic or aromatic and may carry one or more substituents, such as those named in connection with the acetylenically and olefinically unsaturated compounds.

Carboxylic acids preferably used in the process according to the invention include those containing up to 20 carbon atoms. One or more carboxylic acid groups may be present, thus allowing various products as desired, depending on the molar ratio of the reactants used. The carboxylic acids may, for example, be alkanecarboxylic acids or alkenecarboxylic acids. Examples of carboxylic acids are: formic acid, acetic acid, propionic acid, n-butyric acid, isobutyric acid, pivalic acid, n-valeric acid, n-caproic acid, caprylic acid, capric acid, lauric acid, myristic acid, palmitic acid, stearic acid, benzoic acid, o-phthalic acid, m-phthalic acid, terephthalic acid and toluic acid. Examples of alkenecarboxylic acids are acrylic acid, propiolic acid, methacrylic acid, crotonic acid, isocrotonic acid, oleic acid, maleic acid, fumaric acid, citraconic acid and mesaconic acid.

A silanol is preferably a trialkylsilanol, more preferably a tri($C_{1-6}$)alkylsilanol such as triethylsilanol.

It will be appreciated that the unsaturated hydrocarbon and the hydroxyl-containing compound may be the same compound.

When an acetylenically unsaturated compound is reacted with water and carbon monoxide, an alpha,-beta-unsaturated carboxylic acid is formed. If an alcohol is used instead of water, an alpha,beta-unsaturated carboxylic ester is formed. If a carboxylic acid is used instead of water, an alpha,beta-unsaturated anhydride is formed. The alpha,beta-unsaturated product may undergo further reaction depending upon the reaction conditions employed.

When an olefinically unsaturated compound is reacted with carbon monoxide and water, a carboxylic acid is formed. If an alcohol is used instead of water, a carboxylic ester is formed: for example reaction of ethene, carbon monoxide and water affords methyl propionate, if a carboxylic acid is used instead of water, an anhydride is formed: for example reaction of ethene, carbon monoxide and propionic acid affords propionic anhydride. If a silanol is used instead of water, a silyl ester is obtained: for example reaction of ethene, carbon monoxide and triethylsilanol affords triethylsilyl propionate.

A surprising property of catalyst systems according to the invention is their ability to selectively carbonylate unsaturated compounds with acid sensitive hydroxy compounds such as tertiary alkanols, for example 2-methyl-propan-2-ol (tertiary butanol) and silanols, for example. triethylsilanol.

According to a preferred aspect therefore, the invention provides a process for the carbonylation of an acetylenically or olefinically unsaturated compound, in which an acetylenically or olefinically unsaturated compound is reacted with carbon monoxide and a tertiary alkanol or a silanol in the presence of a catalyst system as defined previously.

The catalyst system according to the invention has also been found to be surprisingly good for the carbonylation of acetylenically unsaturated compound in the presence of allenes. According to a preferred aspect, therefore, the present invention provides a process for the carbonylation of an acetylenically unsaturated compound, in which an acetylenically unsaturated compound is reacted with carbon monoxide in the presence of an allene and a catalyst system as defined above.

Preferably the allene is present in an amount of from 0.3 to 10 per cent by weight, based upon the weight of the acetylenically unsaturated compound.

When an allene is present, the tertiary amine is preferably used in catalytic amounts.

It is not essential to use a separate solvent in the process according to the invention. In some cases, however, it may be desirable to use a separate solvent. Any inert solvent can be used for that purpose. Said solvent may, for example, comprise sulfoxides and sulfones, for example dimethylsulfoxide, diisopropylsulfone or tetrahydrothiophene-2,2-dioxide (also referred to as sulfolane), 2-methylsulfolane, 3-methylsulfolane, 2-methyl-4-butylsulfolane; aromatic hydrocarbons such as benzene, toluene, xylenes; esters such as methylacetate and butyrolactone; ketones such as acetone or methyl isobutyl ketone, ethers such as anisole, 2,5,8-trioxanonane (also referred to as diglyme), diphenyl ether and diisopropyl ether, and amides such as N,N-dimethylacetamide or N-methylpyrrolidone.

The process according to the present invention is conveniently effected at a temperature in the range of from 10° C. to 200° C., in particular from 20° C. to 130° C.

The process according to the invention is preferably effected at a pressure of from 1 to 100 bar. Pressures higher than 100 bar may be used, but are generally economically unattractive on account of special apparatus requirements.

The molar ratio of the hydroxyl-containing compound to the unsaturated hydrocarbon may vary between wide limits and generally lies within the range of 0.01:1 to 100:1.

The carbon monoxide required for the process according to the present invention may be used in a practically pure form or diluted with an inert gas, for example nitrogen. The presence of more than small quantities of hydrogen in the gas stream is undesirable on account of the hydrogenation of the unsaturated hydrocarbon which may occur under the reaction conditions. In general, it is preferred that the quantity of hydrogen in the gas stream supplied is less than 5 vol %.

The catalyst systems used in the process according to the invention are constituted in a liquid phase. They may be prepared by any convenient method. Thus they may be prepared by combining a separate Group VIII metal compound, the phosphine (I), the protonic acid and the tertiary amine in a liquid phase. Alternatively, they may be prepared by combining a Group VIII metal compound and an acid addition salt of the phosphine and the tertiary amine in a liquid phase. Alternatively, they may be prepared from a Group VIII metal compound which is a complex of a Group VIII metal with the phosphine, the protonic acid and the tertiary amine in a liquid phase. Alternatively, they may be prepared by combining a Group VIII metal compound, the phosphine and an acid addition salt of the tertiary amine in a liquid phase.

The liquid phase may conveniently be formed by one or more of the reactants with which the catalyst system is to be used. Alternatively, it may be found by a solvent. It may also be found by one of the components of the catalyst system, for example a tertiary amine.

Phosphines having an aromatic substituent which contains an imino nitrogen atom are known in the art. They are conveniently prepared by reacting a phosphorus halide or alkali metal phosphide with a appropriate alkali metal or halide derivative of an aromatic compound containing an imino nitrogen atom.

The invention will now be further described by the following examples which are illustrative and which are not intended to be construed as limiting the scope of the invention.

PREPARATION 1

Preparation of diphenyl-(6-methyl-2-pyridyl)-phosphine

All manipulations were carried out in an inert atmosphere (nitrogen or argon). Solvents were dried and distilled prior to use. 36 ml of a 1.6M n-butyllithium solution in hexane was added to 40 ml diethyl ether, and the mixture was cooled to −40° C. To the stirred mixture was added in the course of 20 minutes a solution of 10 g 2-bromo-6-methylpyridine in 15 ml diethyl ether; during this addition, the temperature was kept at −40° C. After the addition, the temperature was raised to −5° C., kept there for 5 minutes, and then lowered again to −40° C. A solution of 12.8 g chlorodiphenylphosphine in 15 ml diethyl ether was added in the course of 15 minutes to the stirred mixture. After the addition, the mixture was warmed to room temperature, the solvents were removed in vacuo, and 50 ml water and 50 ml dichloromethane were added. After 5 minutes of vigorous stirring, the dichloromethane layer was separated. The water layer was extracted with two 50 ml portions of dichloromethane, the organic reactions were combined, and the solvent removed in vacuo. The residue was crystallized from toluene/hexane to afford 12 g (75%) of diphenyl-(6-methyl-2-pyridyl)-phosphine as off-white crystals. The product was characterized by $^{31}P$ NMR: $\delta_p = -5.6$ ppm.

PREPARATION 2

Preparation of diphenyl-(3-methyl-2-pyridyl)-phosphine

This compound was prepared as described in Preparation 1, but using 10.0 g of 2-bromo-3-methylpyridine instead of the 2-bromo-6-methylpyridine. It was characterized by $^{31}P$ NMR: $\delta_p = -8.1$ ppm.

PREPARATION 3

Preparation of phenyl-bis(6-methyl-2-pyridyl)-phosphine

This compound was prepared as described in Preparation 1, but using 5.2 g of phenyldichlorophosphine instead of the chlorodiphenylphosphine. It was characterized by $^{31}P$ NMR: $\delta_p = -5.1$ ppm.

PREPARATION 4

Preparation of tris(6-methyl-2-pyridyl)-phosphine

This compound was prepared as described in Preparation 1, but using 2.7 g of phosphorus trichloride instead of the chlorodiphenylphosphine. It was characterized by $^{31}P$ NMR: $\delta_p = -3.8$ ppm.

PREPARATION 5

Preparation of diphenyl-(4,6-dimethyl-2-pyridyl)-phosphine

This compound was prepared as described in Preparation 1, but using 10.8 g of 2-bromo-4,6-dimethylpyridine instead of the 2-bromo-6-methylpyridine. It was characterized by $^{31}P$ NMR: $\delta_p = -5.6$ ppm.

PREPARATION 6

Preparation of diphenyl-(6-methoxy-2-pyridyl)-phosphine 2.7 g Sodium was added to 100 ml liquid ammonia at −80° C., and then 15.2 g of triphenylphosphine was added in 6 portions with stirring. The solution was slowly warmed to −40° C., kept at that temperature for 30 min. and then cooled again to −80° C. Then, 3.1 g of ammonium chloride was added to the stirred solution, followed by 10.9 g of 2-bromo-6-methoxypyridine in three portions. The cooling bath was removed and the ammonia was allowed to evaporate. The residue was worked up with water/dichloromethane as described in Preparation 1. Crystallization from hexane afforded 7 g of a somewhat impure product (characterized by $^{31}P$ NMR: $\delta_p = -4.4$ ppm) which was used as such in the following Examples.

PREPARATION 7

Preparation of di(n-butyl)-2-pyridyl phosphine

To a magnetically stirred solution of 2.5 g phenyl(2-pyridyl)$_2$P in 20 mol tetrahydrofuran, cooled to −80° C., was added in the course of 10 min 5.9 ml of a 1.6M solution of n-butylLi in hexane. The resulting deep-red solution was allowed to warm to room temperature, and analysis of the solution by $^{31}P$ NMR showed it to contain the phosphide (n-butyl)(2-pyridyl)PLi as the only phosphorus-containing compound ($\beta_p = -16.3$ ppm).

The solution was cooled to −40° C. and a solution of 1.3 g 1-bromobutane in 10 ml tetrahydrofuran was added. The mixture was again warmed to room temperature, the solvents were removed in vacuo, and 25 ml of diethylether and 10 ml of water were added. After 10 minutes of stirring, the organic layer was separated and the water layer was extracted with 10 ml of ether. The organic layers were combined and the solvent was removed in vacuo (66 Pa). The resulting light-yellow liquid was analyzed by $^1H$, $^{13}C$ and $^{31}P$ NMR and shown to consist of a 1:1 (molar ratio) mixture of 2-phenylpyridine and (n-butyl)$_2$(2-pyridyl)P ($\delta_p = -19.5$ ppm).

PREPARATION 8

Preparation of dimethyl 2-pyridyl phosphine and methylphenyl-2-pyridyl phosphine The method of Preparation 7 was repeated, except that a 1.6M solution of methylLi in diethylether was used instead of the n-butylLi solution, and 1.3 g of iodomethane instead of the bromobutane. The reaction product was a mixture of (methyl)₂ 2-pyridyl)P, methyl phenyl 2-pyridylP and 2-phenyl pyridine in the approximate ratio 70:30:60, from which the (methyl)₂(2-pyridyl)P was isolated by distillation.

The physical characteristics of the products were $\delta_p = -41.2$ ppm (dimethyl-2-pyridylphosphine) and $\delta_p = -24.1$ ppm (methylphenyl-2-pyridylphosphine).

PREPARATION 9

Preparation of n-butyl tert-butyl 2-pyridyl phosphine

The method of Preparation 7 was repeated, except that 5.6 ml of a 1.7M solution of t-butylLi in pentane was used instead of the n-butylLi solution. The final product was identified as n-butyl t-butyl 2-pyridylP by NMR analysis ($\delta p = -7.4$ ppm).

PREPARATION 10

Preparation of dimethyl 2-pyridylphosphine

The method of Preparation 8 was repeated, except that 1.91 g methyl(2-pyridyl)₂P and only 0.7 g iodomethane were used. Workup as described in Example 1 afforded dimethyl 2-pyridyl phosphine, which was further purified by distillation (65% yield). ($\delta_p = -41.2$ ppm).

PREPARATION 11

Preparation of n-butyl(4-methoxyphenyl)(2-pyridyl)phosphine

All manipulations were carried out in an inert atmosphere (nitrogen or argon). Solvents were dried and distilled prior to use. 18 ml of a 1.6M n-butyllithium solution in hexane was added to 30 ml diethyl ether, and the mixture was cooled to −40° C. To the stirred mixture was added in the course of 20 minutes a solution of 4.6 g 2-bromopyridine in 15 ml diethyl ether, during this addition, the temperature was kept at −40° C. After the addition, the temperature was raised to −5° C., kept there for 5 minutes, and then lowered again to −40 ° C. The resulting solution was added to a cooled (−40° C.) solution of 7.6 g 4-methoxyphenyl-bis(2-pyridyl)phosphine in 30 ml THF. The mixture was warmed to room temperature. After stirring for 10 minutes, the solvents were removed in vacuo. Water (25 ml) and dichloromethane (25 ml) were added. After 5 minutes of vigorous stirring, the dichloromethane layer was separated. The water layer was extracted with two 25-ml portions of dichloromethane, the organic fractions were combined, and the solvent removed in vacuo. The residue was distilled, giving 4.7 g (60%) of (n-butyl) (4-methoxyphenyl) (2-pyridyl) phosphine as a yellowish liquid. The product was characterized by ³¹P NMR:$\delta_p = -14.9$ ppm.

In this experiment, n-butyllithium is believed to react with 2-bromopyridine to afford a mixture of n-butylbromide and 2-pyridyllithium. Then the 2-pyridyllithium reacts with 4-methoxy-bis(2-pyridyl)phosphine to afford 4-methoxyphenyl(2-pyridyl)lithium phosphide (and 2,2'-bipyridine). The lithium phosphide then reacts with n-butylbromide to afford (n-butyl) (4-methoxyphenyl)(2-pyridyl)phosphine.

PREPARATION 12

Preparation of methyl di(2-pyridyl)phosphine

All manipulations were carried out in an inert atmosphere (nitrogen or argon). Solvents were dried and distilled prior to use. 36 ml of a 1.6M n-butyllithium solution in hexane was added to 40 ml diethyl ether, and the mixture was cooled to −40° C. To the stirred mixture was added in the course of 20 minutes a solution of 9.2 g 2-bromopyridine in 15 ml diethyl ether; during this addition, the temperature was kept at −40° C. After the addition, the temperature was raised to −5° C., kept there for 5 minutes, and then lowered again to −40° C. A solution of 3.4 g methyldichlorophosphine in 15 ml diethyl ether was added to the stirred mixture. After the addition, the mixture was warmed to room temperature, the solvents were removed in vacuo, and 50 ml water and 50 ml dichloromethane were added. After 5 minutes of vigorous stirring, the dichloromethane layer was separated. The water layer was extracted with two 50-ml portions of dichloromethane, the organic fractions were combined, and the solvent removed in vacuo. The residue was distilled, giving 4.0 g (68%) of methyl-bis(2-pyridyl)phosphine as a yellowish liquid. The product was characterized by ³¹P NMR:$\delta_p = -20.5$ ppm.

EXAMPLE 1

A 250 ml stainless steel magnetically stirred autoclave was filled with 0.1 mmol palladium(II)acetate, 5 mmol bisphenyl(2-pyridyl)phosphine, 4 mmol paratoluenesulfonic acid, 50 ml (620 mmol) pyridine and 10 ml (65 mmol) triethylsilanol. Air was then evacuated from the autoclave, and then carbon monoxide (30 bar) and ethylene (20 bar) were added. The autoclave was then sealed and heated to a temperature of 110° C. After a reaction time of 4.5 hours, a sample of the contents of the autoclave was withdrawn and analyzed by gas liquid chromatography.

Triethylsilylpropionate was formed with a selectivity of 60% (based on silanol). Di-triethylsilyl ether was also formed, with a selectivity of about 40% (based on silanol). The mean conversion rate was calculated to 200 mol ethene/gram atom Pd/hour.

COMPARATIVE EXAMPLE A

The method of Example 1 was repeated, but using triphenylphosphine instead of bisphenyl(2-pyridyl)phosphine, and withdrawing a sample of the contents of the autoclave after 5 hours instead of 4.5 hours. Only traces of triethylsilyl propionate were detected.

COMPARATIVE EXAMPLE B

The method of Comparative Example A was repeated, but using 50 ml methylpropionate instead of 50 ml pyridine and heating to 80° C. instead of 110° C. Di(triethylsilyl)ether was formed with a selectivity of >90%. Only traces of triethylsilylpropionate were detected.

EXAMPLE 2

A 250 ml stainless steel, magnetically stirred autoclave was filled with 0.1 mmol palladium(II)acetate, 5 mmol bisphenyl(2-pyridyl)phosphine, 4 mmol p-toluenesulfonic acid, 40 ml (500 mmol) pyridine, 20 ml methanol and 5 g paraformaldehyde. Air was then evacuated from the autoclave, and then carbon monoxide (30 bar) and ethene (20 bar) were added. The autoclave was then sealed and heated to a temperature of 110° C. After a reaction time of 5 hours, a sample of the contents of the autoclave was withdrawn and analyzed by gas liquid chromatography. Two products were found; methoxymethylpropionate, which had been formed with a selectivity of 10%, and methylpropionate, which had been formed with a selectivity of 90%. The mean reaction rate was calculated to be 200 mol ethene/gram atom Pd/hour.

COMPARATIVE EXAMPLE C

The method of Example 2 was repeated, but using triphenylphosphine instead of bisphenyl(2-pyridyl)phosphine. Only traces of carbonylated products were observed.

COMPARATIVE EXAMPLE D

The method of Example 2 was repeated, but using no pyridine, and 50 ml methanol instead of 20 ml methanol. The sample of the contents of the autoclave was withdrawn after a reaction time of 2 hours. Only traces of methoxymethylpropionate were observed. Methylpropionate was found to have been formed with a selectivity of >95%. The mean reaction rate was calculated to be 1000 mol ethene/gram atom Pd/hour.

EXAMPLE 3

The method of Example 2 was repeated but using 40 ml (350 mmol) 2,6-dimethylpyridine instead of 40 ml pyridine, heating to 125° C. instead of 110° C., and analyzing a sample of the contents of the autoclave after 4.5 hours instead of 5 hours. Methoxymethylpropionate was found to have been formed with a selectivity of 35%. and methylpropionate with a selectivity of 60%. The mean reaction rate was calculated to be 150 mol ethene/gram atom Pd/hour.

EXAMPLE 4

The method of Example 2 was repeated, but using 40 ml (350 mmol) 2,6-dimethylpyridine instead of pyridine, 10 ml methanol instead of 20 ml methanol and heating to 125° C. instead of 110° C. Methoxymethylpropionate was found to have been formed with a selectivity of 60%, and methyl propionate with a selectivity of 30%. The mean reaction rate was calculated to be 100 mol ethene/gram atom Pd/hour.

EXAMPLE 5

A 250 ml stainless steel magnetically stirred autoclave was filled with 0.1 mmol palladium(II)acetate, 2 mmol bisphenyl(2-pyridyl)phosphine, 10 mmol paratoluenesulfonic acid, 40 ml (500 mmol) pyridine and 20 ml methanol. Air was then evacuated from the autoclave and then 20 bar ethene and 30 bar carbon monoxide were added. The autoclave was then sealed and heated to 110° C. After a reaction time of 5 hours, a sample of the contents of the autoclave was withdrawn and analyzed by gas liquid chromatography. Methylpropionate was found to have been formed. The mean reaction rate was calculated to be 300 mol ethene/gram atom Pd/hour. No methyltriphenylphosphonium tosylate was detected, indicating that the catalyst had remained stable during the course of the reaction.

COMPARATIVE EXAMPLE E

The method of Example 5 was repeated but using triphenylphosphine instead of bisphenyl(2-pyridyl)phosphine. Methyl propionate was detected, but the mean reaction rate was calculated to be less than 10 mol ethene/gram atom Pd/hour.

COMPARATIVE EXAMPLE F

The method of Example 5 was repeated, but using tris(p-chlorophenyl)phosphine instead of bisphenyl(2-pyridyl)phosphine, 4 mmol paratoluenesulfonic acid, heating to 130° C., and withdrawing a sample from the autoclave after 4 hours. Methyl propionate was detected. The mean reaction rate was calculated to be less than 10 mol ethene/gram atom Pd/hour.

EXAMPLE 6

The method of Example 5 was repeated, but using 40 ml (320 mmol) N,N-dimethylaniline instead of 40 ml pyridine heating to 100° C. instead of 110° C., and withdrawing a sample from the autoclave after 1½ hour instead of 5 hours. Methyl propionate had been formed. The mean reaction rate was calculated to be 700 mol ethene/gram atom Pd/hour.

EXAMPLE 7

The method of Example 5 was repeated, but using 20 ml (270 mmol) propionic acid instead of 20 ml methanol, and heating to 90° C. instead of 110° C. Propionic anhydride was formed. The mean reaction rate was calculated to be 250 mol ethene/gram atom Pd/hour.

EXAMPLE 8

The method of Example 5 was repeated, but using 5 mmol bisphenyl(2-pyridyl)phosphine, 4 mmol paratoluenesulfonic acid, 30 ml methanol, and heating for 3 hours instead of 5 hours. Methyl propionate was formed. The mean conversion rate was calculated to be 800 mol ethene/gram atom Pd/hour.

EXAMPLE 9

The method of Example 5 was repeated, but using 5 mmol bisphenyl(2-pyridyl)phosphine, 4 mmol trifluoromethanesulfonic acid, and withdrawing a sample of the contents of the autoclave after 3 hours. Methyl propionate was formed. The mean reaction rate was calculated to be 1000 mol ethene/gram atom Pd/hour.

EXAMPLE 10

The method of Example 5 was repeated, but using 5 mmol bisphenyl(2-pyridyl)phosphine, 4 mmol paratoluenesulfonic acid, 50 ml methanol instead of 20 ml, and 10 g (95 mmol) poly-4-vinylpyridine (cross-linked) instead of 40 ml pyridine. Methyl propionate was formed. The mean reaction rate was calculated to be 400 mol ethene/gram atom Pd/hour.

EXAMPLE 11

A 300 ml magnetically-stirred stainless steel autoclave was successively filled with 0.025 mmol palladium(II)acetate, 1 mmol bisphenyl (6-methyl-2-pyridyl)phosphine, 2 mmol 2-methyl-2-propylsulfonic acid, 30 ml methyl methacrylate as solvent, 30 ml methanol and 10 mmol dimethylaniline. Air was then evacuated from the autoclave, and then 30 ml propyne containing 0.4% allene was added. Carbon monoxide was then added to a pressure of 60 bar. The autoclave was then sealed and heated to a temperature of 60° C. After a reaction time of 0.1 hour at 60° C., a sample of the contents of the autoclave was analyzed by gas liquid chromatography. From the results of the analysis, the selectivity to methyl methacrylate was calculated to be 99.94% and the mean conversion rate was calculated to be 90,000 mol propyne/gram atom Pd/hour.

EXAMPLE 12 TO 18 AND COMPARATIVE EXAMPLE G

The method of

EXAMPLE 11 was repeated using different tertiary amines, and different amounts of allene in the propyne. The results are summarized in Table 1.

The results demonstrate that the inhibitory effect of allene on the catalyst can be counteracted by using tertiary amines.

TABLE 1

| Example | Ligand (mmol) | Acid (mmol) | Solvent | Promoter (mmol) | % allene | Temp (°C.) | Selectivity (%) | Mean Conversion rate (mol propyne/gat.Pd/hr) |
|---|---|---|---|---|---|---|---|---|
| 11 | 2-P$\phi_2$-6-methylpyridine (1) | $CH_3SO_3H$ (2) | MMA | $C_6H_5$-$N(CH_3)_2$ (10) | 0.4 | 60 | 99.94 | 90,000 |
| 12 | 2-P$\phi_2$-pyridine (1) | $CH_3SO_3H$ (2) | MMA | $CH_3$-$C_6H_4$-$N(CH_3)_2$ (2.5) | 0.4 | 60 | 99.0 | 67,000 |
| 13 | 2-P$\phi_2$-6-methylpyridine (1) | $CH_3SO_3H$ (2) | MMA | $CH_3$-$C_6H_4$-$N(CH_3)_2$ (20) | 0.4 | 60 | 99.94 | 18,000 |
| 14 | 2-P$\phi_2$-6-methylpyridine (1) | $CH_3SO_3H$ (2) | MMA | 2,6-di-tert-butylpyridine (2.5) | 0.4 | 60 | 99.9 | 30,000 |
| 15 | 2-P$\phi_2$-6-methylpyridine (1) | $CH_3SO_3H$ (2) | MMA | 3,4-dimethylpyridine (2.5) | 0.4 | 60 | 99.9 | 9,000 |
| 16 | 2-P$\phi_2$-6-methylpyridine (1) | $CH_3SO_3H$ (2) | MMA | 2,6-dichloropyridine (2.5) | 0.4 | 60 | 99.9 | 15,000 |
| 17 | 2-P$\phi_2$-6-methylpyridine (1) | $CH_3SO_3H$ (2) | MMA | $CH_3$-$C_6H_4$-$N(CH_3)_2$ (10) | 2.0 | 60 | 99.9 | 7,000 |

TABLE 1-continued

Carbonylation of Propyne and Methanol to give methyl methacrylate

| Example | Ligand (mmol) | Acid (mmol) | Solvent | Promoter (mmol) | % allene | Temp (°C) | Selectivity (%) | Mean Conversion rate (mol propyne/gat.Pd/hr) |
| --- | --- | --- | --- | --- | --- | --- | --- | --- |
| 18 | 6-methyl-2-(diphenylphosphino)pyridine (3) | $(CH_3)_3CSO_3H$ (2) | MMA | $CH_3$—C$_6H_4$—$N(CH_3)_2$ (10) | 7.0 | 45 | 99.9 | 6,000 |
| G | 2-(diphenylphosphino)pyridine (1) | $CH_3SO_3H$ (2) | MMA | None | 0.4 | 60 | 98.9 | 7,000 |

Key
MMA Methylmethacrylate
φ Phenyl group

What is claimed is:

1. A catalyst system which comprises:
   a) a Group VIII metal compound;
   b) a phosphine having an aromatic substituent which contains an imino nitrogen atom;
   c) a protonic acid; and
   d) a tertiary amine selected from the group consisting of a pyridine and an N,N-dialkylaniline.

2. The catalyst system of claim 1 wherein the Group VIII metal compound is a palladium compound.

3. The catalyst system of claim 2 wherein an imino group in an aromatic substituent containing an imino nitrogen atom is linked to a phosphorus atom through a single bridging carbon atom.

4. The catalyst system of claim 3 wherein the phosphine is selected from the group consisting of 2-pyridyl, 2-pyrimidyl and 2-triazinylphosphine.

5. The catalyst system of claim 1 wherein the number of equivalents of tertiary amine per mole of protonic acid is at least 1.

6. The catalyst system of claim 5 wherein the number of equivalents of tertiary amine per mole of protonic acid is in the range of from 1.5 to 1,500.

* * * * *